United States Patent
Vessey et al.

(10) Patent No.: US 8,252,720 B2
(45) Date of Patent: Aug. 28, 2012

(54) **USE OF *GLUCONACETOBACTER* WITH REDUCED USE OF NITROGEN FERTILIZER TO IMPROVE BEET CROP PRODUCTION**

(76) Inventors: J. Kevin Vessey, Hammonds Plains (CA); Houman Fei, Beechville (CA); Abuduxikuer Abudureheman, Halifax (CA)

( * ) Notice: Subject to any disclaimer, the term of this patent is extended or adjusted under 35 U.S.C. 154(b) by 0 days.

(21) Appl. No.: 13/035,252

(22) Filed: Feb. 25, 2011

(65) Prior Publication Data

US 2011/0225679 A1    Sep. 15, 2011

Related U.S. Application Data

(63) Continuation-in-part of application No. PCT/CA2009/001200, filed on Aug. 31, 2009.

(60) Provisional application No. 61/092,939, filed on Aug. 29, 2008.

(51) Int. Cl.
*A01N 63/00* (2006.01)
(52) U.S. Cl. ..................................... 504/117
(58) Field of Classification Search .................. None
See application file for complete search history.

(56) References Cited

U.S. PATENT DOCUMENTS

| 5,641,667 A | 6/1997 | Sosa et al. |
| 5,731,173 A | 3/1998 | Sosa et al. |

FOREIGN PATENT DOCUMENTS

| JP | 2006248898 A | 9/2006 |
| JP | 2006340624 A | 12/2006 |
| WO | WO 02/45513 A2 | 12/2002 |

OTHER PUBLICATIONS

Vessey et al. (Improved sugar beet production following inoculation by *Gluconacetobacter* ssp., Poster, 11 International Symposium on Nitrogen Fixation in Non Legumes, Gent, Belguim, 2008).*
Adriano-Anaya ML et al. (2006) "Hydrolytic enzyme activities in maize (*Zea mays*) and Sorghum (*Sorghum bicolor*) roots inoculated with *Gluconacetobacter diazotrophicus* and *Glomus intraradices*" Soil Biology & Biochemistry, 38: 879-886.

Paula MA et al. (1992) "Synergistic effects of vesicular-arbuscular mycorrhizal fungi and diazotrophic bacteria on nutrition and growth of sweet potato (*Ipomoea batatas*)" Biology and Fertility of Soils, 14(2):61-66.
Pedraza RO, (2008) "Recent advances in nitrogen-fixing acetic acid bacteria" International Journal of Food Microbiology, 125(1): 25-35.
Sahin F et al. (2004) "Sugar beet and barley yields in relation to inoculation with N2-fixing and phosphate solubilizing bacteria," Plant Soil, 265: 123-129.
Saravanan VS et al. (2008) "Ecological occurrence of *Gluconacetobacter diazotrophicus* and nitrogen-fixing *Acetobacteraceae* members: their possible role in plant growth promotion." Microbial Ecology. 55(1):130-140.
Sevilla M et al. (2001) "Comparison of benefit to sugarcane plant growth and 15N2 incorporation following inoculation of sterile plants with *Acetobacter diazotrophicus* wild-type Nif-mutant strains" Molecular Plant-Microbe Interactions, 14(3): 358-366.
Vessey K et al. (Sep. 4, 2008) "Improving sugar beet as a bioethanol feedstock crop with endophytic diazotrophs" Abstract, 11th International Symposium on Nitrogen Fixation in Non-Legumes, Gent, Belgium, 42 of Abstract Book (online: http://nfix2008.psb.ugent.be/files/Abstractboek11th.pdf).
Vessey K et al. (Sep. 4, 2008) "Improved sugar beet production following inoculation by *Gluconaceterbacter* spp" Poster, 11th International Symposium on Nitrogen Fixation in Non-Legumes, Gent, Belgium.
Vessey K et al. (Jun. 19, 2009) "Enhancement of Growth and Nitrogen Accumulation in Sugar Beet by Inoculation with *Gluconacetobacter diazotrophicus*" 16th International Congress on Nitrogen Fixation, Big Sky, Montana.
Wegner JP et al. (Nov. 2008) "Danisco sugar's first beet-based bioethanol plant" International Sugar Journal, 110 (1319): 697-700.
Youssef HH et al. (2004). "*Gluconacetobacter diazotrophicus*: a natural endophytic diazotroph of Nile Delta sugarcane capable of establishing an endophytic association with wheat" Biology and Fertility of Soils. 39(6): 391-397.
ATCC Biological Deposit: *G. diazotrophicus* PAL5T, ATCC No. 49037.

* cited by examiner

*Primary Examiner* — Alton Pryor
(74) *Attorney, Agent, or Firm* — Bereskin & Parr LLP/S.E.N.C.R.L., s.r.l.; Noel Courage

(57) ABSTRACT

There is provided an inoculant composition for sucrose-rich crops improving production with reduced use of nitrogen fertilizer, which comprises *Gluconacetobacter* in suspension in a suitable culture medium, wherein the *Gluconacetobacter* being in an amount suitable for inoculation of the crops. There is also provided, a method for improving production of sucrose-rich crops with reduced use of nitrogen fertilizer, which comprises inoculating the sucrose-rich crop with the *Gluconacetobacter* inoculant composition.

23 Claims, 1 Drawing Sheet

USE OF *GLUCONACETOBACTER* WITH REDUCED USE OF NITROGEN FERTILIZER TO IMPROVE BEET CROP PRODUCTION

CROSS REFERENCE TO RELATED PATENT APPLICATIONS

This application is a continuation-in-part of PCT application no. PCT/CA2009/001200, filed Aug. 31, 2009, which claims priority from U.S. patent application No. 61/092,939, filed Aug. 29, 2008, both of which are incorporated herein by reference in their entirety.

INCORPORATION OF SEQUENCE LISTING

A computer readable form of the Sequence Listing "15102-16_SequenceListing.txt" (1,095 bytes), submitted via EFS-WEB and created on May 19, 2011, is herein incorporated by reference.

BACKGROUND (a) Field

The invention relates to a bacterial inoculant composition to improve production of sucrose-rich crops with reduced use of nitrogen fertilizer.

(b) Description of Prior Art

Nitrogen is an essential plant nutrient for plant growth, being an indispensable building block of amino and nucleic acids.

Nitrogen-based fertilizers, which are inorganic fertilizers, are most commonly used to treat fields used for growing maize, followed by barley, sorghum, rapeseed, soybean and sunflower. Nitrogen fertilizer is often synthesized using the Haber-Bosh process, which produces ammonia. This ammonia is then used to produce other compounds, notably anhydrous ammonium nitrate and urea, which can be applied to fields.

High application rates of inorganic nitrogen fertilizers in order to maximize crop yields, combined with the high solubility of these fertilizers, lead to increased leaching of nitrates into groundwater (C. J. Rosen and B. P. Horgan, *Preventing Pollution Problems from lawn and garden fertilizers*, 2009, *University of Minessota Extention*). Eventually, nitrate-enriched groundwater will make its way into lakes, bays and oceans where it accelerates the growth of algae, disrupts the normal functioning of water ecosystems, and kill fish in a process called euthrophication. The use of ammonium nitrate in inorganic fertilizers is particularly damaging, as plants absorb ammonium ions preferably to nitrate ions. This allows excess nitrate ions which are not absorbed to be freely dissolved (by rain or irrigation) into groundwater and other waterways, leading to euthrophication.

Application of nitrogen fertilizer to plants to increase their productivity can have negative and unpredictable effects on the environment (Di and Cameron, *Nutrient Cycling in Agroecosystems* 46:237-256, 2002) (Erisman et al., *Environmental Pollution*, 150:140, 149, 2007). However, biological nitrogen fixation ("BNF") has a significant effect on improving yield of sugar beet, which lowers the cost of beet production and increases its chance of being efficient biofuel feedstock in temperate regions.

Therefore, it would be highly desirable to obtain a composition allowing improved production of plants with reduced use of nitrogen fertilizer.

Some limited attempts to infect novel plant host species with endophytic diazotrophs have been made. No evidence of commercially adequate $N_2$ fixation or growth stimulations by these bacteria within the new hosts is was obtained.

There are reports of positive yield responses of sugar beet inoculation with $N_2$-fixing strains of *Bacillus* (Sahin et al. 2004, Plant Soil 265:123; Cakmakci et al. 2006, Biol Biochem 38:1482). However, there remains a need for better strains of $N_2$-fixing bacteria that can colonize sugar beet and reduce fertilizer requirements.

SUMMARY OF THE INVENTION

The application provides a composition comprising *Gluconacetobacter* in suspension in a suitable culture medium to improve the production of a sucrose-rich plant with reduced nitrogen fertilizer usage. For example, inoculating sugar beet plants with *Gluconacetobacter* has shown that these bacteria can provide substantial amount of biologically fixed nitrogen to the plant, which increases biomass significantly. The application shows that this effect is reproducible across *Gluconacetobacter*. In one example, a large sample of 14 different species of *Gluconacetobacter* all improved sugar beet growth. The invention advantageously allows increased sugar beet biomass while using less nitrogen fertilizer. In fact, the bacterium greatly increases the growth and nitrogen accumulation of sugar beet growing under mineral N-deficient conditions. This provides lower cost and less environmental impact. It should be noted that in some cases, the total biomass achieved with a more N-fertilizer efficient plant may not be higher than with a less efficient plant—for example, if more N-fertilizer is provided to a less N-fertilizer efficient plant, it may obtain the same total biomass as a more N-fertilizer efficient plant. However, a significant advantage of the present invention is that the increased N-fertilizer efficiency plants of the invention require administration of less N-fertilizer (eg. at least 10% less, optionally at least 10-25% or 25-50% less N-fertilizer than uninoculated plants) and are therefore much cheaper to produce.

*Gluconacetobacter* is an aerobe and an $N_2$-fixing endophyte that can fix up to 150 kg of N $ha^{-1}$ $year^{-1}$ in sugarcane. The nitrogenase activity of the *Gluconacetobacter* bacterium has a requirement for relatively high concentrations of sucrose to be able to fix nitrogen. Vessey and Pan (2003, Symbiosis 35: 181) showed that in solid-medium culture, *G. diazotrophicus* grows and fixes $N_2$ much better in solid medium containing sucrose than other sugar sources (i.e. glucose and/or fructose). They also showed that the growth rate and $N_2$ fixation rate (as measure by nitrogenase activity) in *G. diazotrophicus* was best when sucrose was in the 1 to 15% range in the medium.

The invention relates to a composition comprising *Gluconacetobacter* in an effective amount to inoculate a sucrose-rich plant, such as a sugar beet plant, and an inoculation medium. Optionally the *Gluconacetobacter* comprises *Gluconacetobacter diazotrophicus* or *Gluconacetobacter johannae*. The *Gluconacetobacter* typically has positive nitrogenase activity as measured by acetylene reduction assay (ARA). The *Gluconacetobacter* in the composition is optionally in a concentration of $10^3$ to $10^8$ CFU/Ml, optionally $10^7$ to $10^8$. The inoculation medium optionally comprises LGI-P. The inoculation medium optionally comprises macroelements from Knop's solutions and microelements from Hoagland's solutions.

Another aspect relates to a kit comprising a composition of the invention in a first container and a nitrogen fertilizer in a second container, the nitrogen fertilizer optionally nitrate, ammonium, urea or anhydrous ammonia. The fertilizer optionally comprises a nitrogen concentration between 1 mM to 10 mM, optionally 2 mM to 5 mM.

Another aspect relates to sucrose rich plant (or progeny thereof), such as a sugar beet, inoculated with a composition of the invention. Optionally, the *Gluconacetobacter* is in the interior of the sugar beet, for example in the hypotocyl, shoot or root of the sugar beet.

Another aspect relates to a method for increasing the biomass of a sucrose rich plant, such as a sugar beet, comprising inoculating the plant with the composition of any of claims 1 to 6 and growing the plant, thereby obtaining increased biomass. The method optionally further comprises administering N-fertilizer to the inoculated plant (eg. sugar beet), wherein the increased biomass is measured as increased biomass per unit of N-fertilizer applied to the inoculated plant compared to a control sugar beet treated with the same amount of N-fertilizer but not treated with the composition. The method optionally further comprises administering N-fertilizer to the inoculated plant (eg. sugar beet), wherein the increased biomass is measured as increased biomass per unit of N-fertilizer applied to the inoculated plant compared to a control plant treated with a larger amount of N-fertilizer but not treated with the composition of the invention, optionally wherein the total biomass yield of the inoculated plant is at least as great, or greater than, as the total biomass yield of the control plant. The *Gluconacetobacter* optionally colonizes the interior of the sugar beet, such as the hypocotyl, shoot or root of the sugar beet. The *Gluconacetobacter* is optionally detected in the interior of the sugar beet by polymerase chain reaction (PCR). The *Gluconacetobacter* is optionally genetically engineered to overexpress a levanase B (lsdB) gene or to underexpress a levansucrase A (lsdA) gene. Another aspect of the invention relates to a method for increasing the biomass of a sugar beet, comprising, consisting essentially of or consisting of: inoculating the sugar beet root tips, root hairs and/or root interface with *Gluconacetobacter* and growing the plant.

In another embodiment, there is provided a method for increasing the N-fertilizer efficiency of a sucrose-rich plant (eg. sugar beet), comprising inoculating the sugar beet with a composition of the invention. Another aspect is method of growing a sugar beet to harvestable maturity in 3 months, optionally 3-4 months, in soil that is in a N-limited condition, comprising inoculating the sugar beet with a composition of the invention and growing the sugar beet to harvestable maturity in 3 months, optionally 3-4 months, in soil that is in a N-limited condition.

The methods useful with respect to sucrose-rich plants are described below with respect to sugar beet, but it should be noted that other plants such as sorghum and sweet potato are also useful in the methods. The inoculating step optionally comprises contacting the composition with the sugar beet or a sugar beet substrate, optionally soil, proximate to the sugar beet so that the composition will contact the sugar beet in the substrate, optionally contacting the sugar beet with sugar beet, sugar beet seed, the soil surrounding the seed or root of the plant, or to the surface of a portion of the sugar beet that is above the substrate. Contacting the composition with the sugar beet seed optionally comprises contacting at seeding or contacting by preinoculation prior to seeding. Optionally, contacting at seeding comprises contacting the seed and/or the substrate surrounding the seed. Contacting at seeding optionally comprises contacting the seed simultaneously with seeding. Contacting by preinoculation prior to seeding optionally comprises coating the seed with a polymer composition following inoculation. Typically, the hypotocyl (beet) of the inoculated sugar beet obtains increased biomass compared to the roots and shoots, when the inoculated sugar beet is compared to an uninoculated sugar beet. The hypotocyl (beet) of the inoclulated sugar beet optionally obtains at least 10% increased biomass compared to the roots and shoots, when the inoculated sugar beet is compared to an uninoculated sugar beet. The substrate is typically soil, sand or a hydroponic solution. The method optionally comprises inoculating the plant at least 15 days after seeding, optionally between 15 to 20 days, optionally 18 days. The plant is optionally inoculated after the first pair of sugar beet leaves open, for example after the cotyledon leaves are fully emerged but before the true leaves are emerged. Optionally the method involves inoculating the plant by applying the composition to the surface of the substrate around a stem of the sugar beet, such as around the base of the stem of the sugar beet. Optionally the method involves growing the sugar beet at least until the plant reaches harvestable maturity, optionally at least 3 months, optionally at least 4 months, from seeding. The method optionally further comprises contacting the sugar beet with a nitrogen fertilizer, optionally daily, optionally with a nitrogen fertilizer containing a nitrogen concentration of 1 mM-10 mM, optionally 2-5 mM. The invention also includes a sugar beet or other sucrose-rich plant inoculated in accordance with a method in this application.

The invention also relates to use of the composition or the kit to inoculate a sugar beet plant or other sucrose-rich plant. The invention also relates to use of the composition or the kit to increase the biomass of the plant, optionally in the presence of reduced nitrogen fertilizer compared to an uninoculated plant. The invention also relates to use of the composition or the kit on sugar beet plant or other sucrose-rich plant for production of sugar beet ethanol.

Another aspect of the invention relates to a method of producing ethanol, comprising fermenting the sugar beet plant or other sucrose-rich plant to produce ethanol and optionally separating the ethanol from the sugar beet. Optionally the method involves obtaining hypocotyl (beet) separated from the sugar beet or other plant and fermenting the hypocotyl and isolating the ethanol from the hypocotyl.

In an embodiment, the invention relates to an inoculant composition for sucrose-rich crops improving production with reduced use of nitrogen fertilizer, which comprises *Gluconacetobacter* in suspension in a suitable culture medium, wherein said *Gluconacetobacter* being in an amount suitable for inoculation of said crops. There is also provided a method for improving the production of a plant by inoculating the plant with the composition of the present invention, as well as uses thereof.

An example of the culture medium comprises at least the following:

| | |
|---|---|
| $K_2HPO_4$ | 0.2 g/L |
| $KH_2PO_4$ | 0.6 g/L |
| $MgSO_4 \cdot 7H_2O$ | 0.2 g/L |
| $CaCl_2 \cdot 2H_2O$ | 0.02 g/L |
| $NaMoO_4 \cdot 2H_2O$ | 0.002 g/L |
| $FeCl_3 \cdot 6H_2O$ | 0.01 g/L |
| 0.5% bromothymol blue solution in 0.2M KOH | 5 ml/L |
| Biotin | 0.1 mg/L |
| Pyridoxal HCl | 0.2 mg/L |
| Sucrose | 100 g/L |
| $(NH_4)_2SO_4$ | 1.32 g/L | pH 5.5 with 1% acetic acid.

The medium for *Gluconacetobacter* culture was modified from the original LGI media (Cavalcante and Dobereiner, Plant Soil 1988: 108:23-31, and Pan and Vessey, Appl. Envir.

Microbiol. 2001, 67:4694-4700). These modifications involved the addition of biotin, pyridoxal HCl and (NH$_4$)$_2$SO$_4$ as described above and the removal of yeast extract from the original formulation. In one embodiment, the application discloses LGI media, the LGI media comprising biotin, pyridoxal salt (optionally pyridoxal HCl) and ammonium salt (optionally (NH$_4$)2SO$_4$). The LGP-1 is typically free from yeast extract. This LGI media typically includes other compounds known for use with LGI media, such as K$_2$HPO$_4$, KH$_2$PO$_4$, MgSO$_4$.7H$_2$O, CaCl$_2$.2H$_2$O, NaMoO$_4$.2H$_2$O, FeCl$_3$.6H$_2$O, bromothymol blue solution in KOH and sucrose. As previously noted, there is provided a method for improving production of sucrose-rich crops with reduced use of nitrogen fertilizer, which comprises inoculating a sucrose-rich crop with an inoculant composition described above.

For the purpose of the present invention the following terms are defined below.

The term "sucrose-rich crop" is intended to include sugar beet (*Beta vulgaris* var. *saccharifera*), sweet potato (*Ipomoea batatas*) and sweet sorghum (*Sorghum bicolor*).

The preferred sucrose-rich crop is sugar beet. Sugar content in sugar beet is typically 17% (fresh weight (FW)), but depends on growth conditions and can often range from 15 to 20% in FW. Sucrose—rich crops are typically at least 10%-15% FW of sucrose, optionally at least 15% FW of sucrose.

The term "hypocotyl" is intended to mean the commercially harvestable "beet" portion of the sugar beet plant.

The term "beet" is intended to mean a portion of the sugar beet anatomically consisting of the hypocotyl and part of the root of the plant.

The term "root" is intended to mean the fibrous root subtending the commercially harvestable beet portion of the sugar beet plant.

BRIEF DESCRIPTION OF THE DRAWINGS

Embodiments of the invention will be described in relation to the drawings in which.

DETAILED DESCRIPTION

Figure 1:
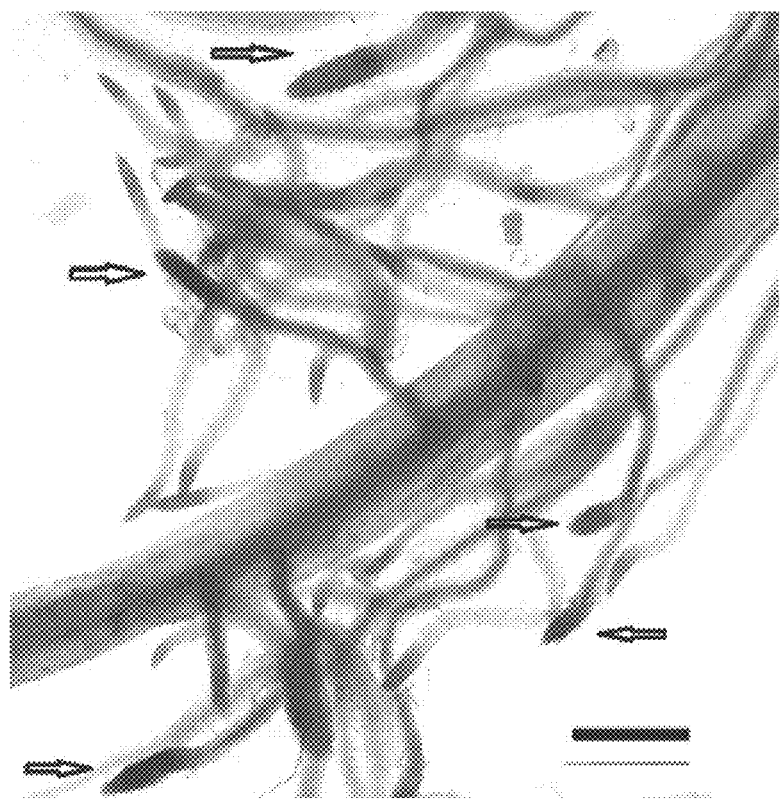
FIG. 1. Light micrograph of lateral root tips of sugar beet were taken 4 days after being inoculated with GUS-labelled *Gluconacetobacter diazotrophicus* UAP-5541/pRGS561. Root tip regions showed blue stain from GUS activity associated with colonization by *G. diazotrophicus* UAP-5541/pRGS561. Bars=1 mm. Mature root hairs also showed blue stain.
Figure 2:
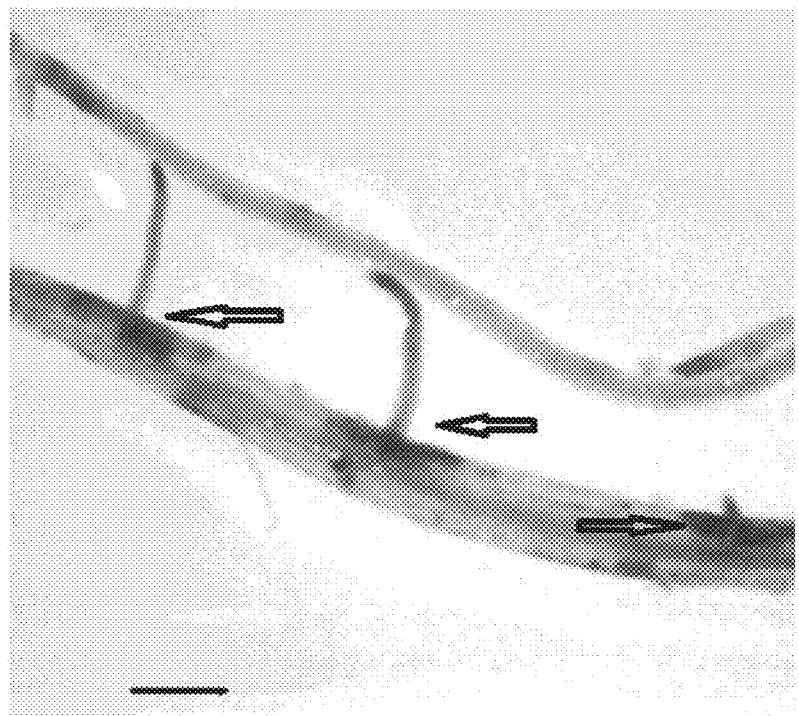
FIG. 2. Light micrograph of lateral root of sugar beet 7 days after being inoculated inoculated with GUS-labelled *Gluconacetobacter diazotrophicus* UAP-5541/pRGS561. Arrows indicating blue stain from GUS activity associated with colonization by *G. diazotrophicus* UAP-5541/pRGS561 at the intersection of lateral roots. Bars=1 mm

The invention provides a composition comprising *Gluconacetobacter* in an effective amount to inoculate sucrose-rich plant, such as a sugar beet. The composition typically includes an inoculation medium that has macroelements (eg. from Knop's solutions) and microelements (eg. from Hoagland's solutions) for supporting *Gluconacetobacter* growth and survival. The *Gluconacetobacter* is optionally cultured in a concentration of $10^3$ to $10^8$ colony forming units (CFU)/ml.

Suitable *Gluconacetobacter* include *Gluconacetobacter diazotrophicus* or *Gluconacetobacter johannae*. Numerous exemplary *Gluconacetobacter* strains are described and tested below. Other *Gluconacetobacter* useful in the present invention are readily identified, for example, by identifying bacteria that test positive in an acetylene reduction assay (ARA) in culture, and then inoculating a plant to verify the effect of the bacteria on the plant.

The invention also relates to a sucrose-rich plant, such as a sugar beet, inoculated with the *Gluconacetobacter* composition. Progeny of the plants, including seeds and seedlings, that retain the inoculated *Gluconacetobacter* are also included within the scope of the invention. The invention provides a significant advantage because inoculation with *Gluconacetobacter* results in the plant colonizing the interior of the plant, not just the surface of the root (as in epiphytes) or the soil around the root (the "rhizosphere" of the roots). The *Gluconacetobacter* optionally colonize the hypotocyl, shoot or root of the plant. The bacteria typically stably colonize the plant even when the plant is at harvestable maturity. The presence of the *Gluconacetobacter* in the interior of the plant is readily verified by detecting *Gluconacetobacter* nucleic acid marker sequences (eg. by PCR) or other *Gluconacetobacter* markers. In certain embodiments, the *Gluconacetobacter* are genetically modified, for example by transfection, to express desirable genes in the bacteria. For example, *Gluconacetobacter* is optionally genetically engineered to overexpress a levanase B (lsdB) gene which further increases plant biomass.

The plants are useful for production of sugar beet ethanol. In one embodiment, the method of producing ethanol, involves fermenting a sucrose-rich plant of the invention, such as sugar beet, in a fermentation medium to produce ethanol. Hypocotyls of sugar beet are typically separated from the full beet before fermentation. The ethanol is then readily separated from the sugar beet, for example by distillation.

The inoculation step is optionally performed by contacting the *Gluconacetobacter* composition with the plant or the plant's substrate (soil is a typical substrate) proximate to the plant so that the composition will contact the plant. The term sugar beet, as used in the methods herein, is intended to include sugar beet seeds and seedlings, whenever appropriate. For example, one may inoculate the soil surrounding the seed or root of the plant, or the surface of a portion of the plant that is above the ground (substrate). For example, one can apply the composition to the surface of the substrate around a stem of a sugar beet. The method of inoculation is convenient because plants can be inoculated with a composition at anytime, optionally at least 15 days, after seeding (seed planting) occurs, optionally between 15 to 20 days, more typically 18 days. A plants is typically inoculated after the first pair of sugar beet leaves open, for example after the cotyledon leaves are fully emerged but before the true leaves are emerged.

Surprisingly, the inventors determined that inoculated sugar beet obtains a greater relative biomass increase in its hypocotyls, when the inoculated sugar beet is compared to an uninoculated sugar beet. The difference in root and shoot gain in the inoculated plants is less dramatic when compared to an uninoculated sugar beet. This is a significant benefit since it is the hypotocyl (beet) that is the commercially harvestable portion of the plant. The hypotocyl of the inoculated sugar beet usefully obtained at least 10%, optionally at least 20%, increased biomass compared to the roots and shoots, when the inoculated sugar beet is compared to an uninoculated sugar beet.

The invention also includes a method for increasing the N-fertilizer efficiency of a sucrose-rich plant, such as a sugar beet, by inoculating the plant with the composition. N-fertilizer efficiency refers to the amount of plant biomass produced per unit of N-fertilizer added to a plant, such as a sugar beet.

For example, increased N-fertilizer efficiency means that increased plant biomass is obtained from a particular plant strain in the presence of a specific amount of N-fertilizer. Since the inoculated plant is able to produce increased biomass per unit of N-fertilizer compared to an uninoculated plant, the inoculated plant has increased N-fertilizer efficiency. Typically, increased N-fertilizer efficiency occurs across the entirety of a plant's structures, although increased N-fertilizer efficiency is readily observed in specific plant parts, such as the hypocotyl, shoot or root. Obtaining increased N-fertilizer efficiency does not mean that the plant's total N-requirements have changed or that they metabolize exogenous N-fertilizer more efficiently—for example, inoculated plants require less N-fertilizer primarily because the *Gluconacetobacter* produce nitrogen from biological N2 fixation—the conversion of N2 gas from the atmosphere into ammonium, a form of N the plant can use. Typically, the inoculated plants do not use less N and will require the same amount of N to grow, develop and for commercial yield as uninoculated crops. The bacterium in the inoculant provides the N from another source so the inoculated plants do not need to absorb as much N from soil and/or fertilizer. A key advantage of the invention remains that the amount of N required to fertilize the crop decreases but one will attain the same yield (because the crop is getting the N through/from the bacteria). The reason the decrease in N fertilizer is so important commercially is because N-fertilizer is the most expensive input in growing a crop.

The methods of the invention typically involve contacting the plant, such as a sugar beet, with a nitrogen fertilizer, for example by fertilizing the plant daily or weekly. The nitrogen fertilizer optionally has a nitrogen concentration of 1 mM-10 mM, optionally 2-5 mM. The composition may be sold by itself or in a kit, for example, in a kit that has a first container that contains the *Gluconacetobacter* in an inoculation medium and a second container that provides nitrogen fertilizer.

Typically, sugar beet are grown in an N-abundant condition. The term "N-abundant condition" typically refers to soil that has over 100 kg N in 1 hectare, typically at least 112 kg N in 1 hectare. The "N-abundant condition" typically refers to the N content at 6 inches (15 cm) deep in the soil. Since the invention advantageously provides sucrose-rich plants with increased N-fertilizer efficiency, these plants can now be grown in soil that contains nitrogen in levels below N-abundant conditions, whether that soil has less nitrogen inherently present or less soil nitrogen after N-fertilizer is added. The plants and methods of the invention provide, for the first time, the ability to grow plants to harvestable maturity in soil that would, prior to this invention, have been considered unacceptably N-limited because they contain inadequate N for commercial production. The term "N-limited condition" refers to soil that contains 70 kg-100 kg of N per hectare, optionally 78 kg-100 kg of N per hectare. The invention typically will allow a decrease in soil N requirements from fertilizer by at least 10% compared to the typical commercial level of at least 112 kg N in 1 hectare (eg. down to 100 kg fertilizer N/ha) and still maintains the same yield of plants at harvestable maturity. Optionally, there is a 25-30% or higher decrease in the amount of N-fertilizer required (eg. 78-84 kg N-fertilizer/ha). The invention therefore relates to a method of growing a sucrose-rich plant in soil that is in a N-limited condition, comprising inoculating the sucrose-rich plant with a composition of the invention and growing the plant. The invention also relates to a method of growing sugar beet in soil that is in a N-limited condition, comprising inoculating the sugar beet with a composition of the invention and growing the sugar beet. Plants may optionally be grown to harvestable maturity in as little as 3 months, optionally 3-4 months. The definitions and amount of N stated in the definitions of "N-abundant" and "N-limited" conditions would be the same in sorghum and sweet potato as for sugar beet.

In the absence of the present invention, plants grown in N-limited soil conditions could become starved for nitrogen which causes physiological differences (e.g. lower levels of protein) which will have negative effects on the plants (grow more slowly, more susceptible to disease, etc). It is clear that N-starved plants will physiologically develop more slowly, but a more significant issue is that the plant will not achieve the same growth rate (ie. how big the plant will get, not how fast it will develop to maturity), and ultimately will not achieve the same yield (ie total biomass or, for example, in the case of sugar beet, hypocotyl biomass), because less nitrogen fertilizer is supplied to them. The invention advantageously provides inoculated plants that require 25-50% less nitrogen fertilizer than a comparable uninoculated plant in order to achieve the same harvestable yield.

Materials and Methods

Fourteen strains of *Gluconacetobacter* were selected for inoculation into sugar beet plants. Also, several plants were not inoculated and served as controls.

The bacterium *Gluconacetobacter* has absolute requirement for relatively high concentrations of sucrose (and not other sugars) to be able to fix nitrogen. It also works in other sucrose-rich crops such as sweet potato (*Ipomoea batatas*) and sweet sorghum (*Sorghum bicolor*).

Plant Growth

Seeds of sugar beet (*Beta vulgaris* L. v. 5451) were germinated in Petri dishes lined with one layer of filter paper wetted with distilled water at room temperature in dark. Seedlings were transferred into 3 L pots containing 3 kg of fine silica sand (one plant/pot). Sand surface in the pots was covered with black landscape cloth.

The plants were grown in a greenhouse with a temperature regime of 25/18° C. (d/n) and with a photoperiod of 16/8 h (d/n). Supplemental light was supplied by HPS (High pressure sodium) lamps at 350-370 $\mu$mol m−2 s−1. Each plant was watered with 100 ml of water daily.

Plants are grown to maturity, which typically means reproductive harvestable maturity. Reproductive harvestable maturity is variable depending on parameters such as availability of sunlight, water and the air temperature. For sugar beets, reproductive maturity typically is at least 3 months after seeding seed germination (ie. planting), eg between 3-4 months. Typical timelines for sweet potato maturity are typically is at least 3 months after seeding (ie. planting), eg between 3-4 months from planting. Typical timelines for sorgum maturity are at least 3 months after seeding (ie. planting), such as between 3-4 months. The physiology of sugar beet, including root morphology, anatomy and gene expression changes as the plant develops. (Milford, 1973, Ann. Appl. Biol. 75: 427; Trebbi and McGrath' 2009, Physiol. Plant. 135: 84; Bellin, et al. 2007, J. Exp. Bot. 58 699). The fact that the effects of the inoculation were observed until harvestable maturity indicates that the positive effects are long lived in the plant and something not just evident in earlier (vegetative, early-reproductive, or mid-reproductive) phases of plant development.

Inoculation

A total of 14 strains of *Gluconacetobacter* spp. (11 strains of *G. diazotrophicus* and 3 strains of *G. johannae*, see Table 1) were cultured with an inoculation medium. The inoculation medium is formulated to support bacterial growth and it delivers the bacteria to the seed or plant. The 14 strains were cultured with LGI-P medium at 30° C. When the first pair of sugar beet leaves opened, 5 ml of the bacterial broth (OD=0.6 at 600 nm; approximately $10^8$ CFU/ml)) was applied to the surface of the sand around the base of each stem of the seedlings. While this is a relatively high dose of bacteria for inoculation of individual plants, lower doses (e.g. at least $10^3$ CFU/ml/plant) are useful to achieve the same results. Experiments indicated that there was no significant difference in plant responses whether the seed and the surface of the sand was inoculated, or just the surface of the sand. It is also reasonable that topical application of inoculant to above ground parts of emerged plant may be an effective means of inoculating the plants. Control plants were not inoculated. After inoculation, the plants were treated with a nutrient solution (macroelements from Knop's, microelements from Hoagland's solutions) containing 1 mM $NO_3^-$ or 10 mM $NO_3^-$, in which there was 1% (w/w) $^{15}N$ in the total N, respectively. "Macroelements" and "microelements" refer to the nutrients needed by the plants. Nutrients required in relatively high amounts, are referred to a macronutrients; relatively low amounts, are micronutrients. Macronutrients include P, K, Ca, Mg; micronutrients include Mn, Bo, Cu, Zn, etc. While NO3– was the form of N used in these studies, other forms of N (anhydrous NH3, NH4+, urea, etc) would have similar effects. By growing the plants at 1 and 10 mM N, we ascertained the potential growth promoting effect of the *Gluconacetobacter* stains at N-deficient (1 mM) and N-sufficient (10 mM) levels of available N. The N-deficiency of the plants grown at 1 mM N is evidenced by the lower growth of these plants (Tables 2, 3, and 4) as compared to those grown at 10 mM N (Tables 5, 5 and 7). There were 5 replicates in each treatment. The inoculated plants were irrigated with 100 ml of the nutrient solution twice a week, and with 100 ml of water in the rest of time. After one month, irrigation volume was 200 ml per plant.

Inoculation of plant seeds is also useful. One typical method is to proceed to seed inoculation at seeding, or just prior to seeding (eg. within hours of going into the ground). The seed coat is often a very difficult place for bacteria to survive, so one typically inoculates the seed, at or just prior to, seeding. Therefore, the methods of the invention therefore include methods using seeds.

Another method of "pre-inoculating" seeds is, for some bacterial inoculants, to enable the seed to be inoculated, days, weeks, or sometimes, even months or more, before seeding. This is optionally done by using special polymers which coat the inoculated seed and enable the bacteria to survive on the seed coat for much longer periods of time (eg. GrowTech Seeds Inc. polymer coating compositions, Boston Mass.).

The plants were harvested after 12 weeks of growth. The shoots, hypocotyls and roots were collected separately, and dried at 80° C. for 3 days.

15-Nitrogen ($^{15}N$) Analysis

The dried tissues were ground into fine powder. $^{15}N$ abundances in all treatments and controls were analyzed by mass spectral meter in Agriculture and Agrifood Canada, Lethbridge.

Sample Protocol for 16S rRNA PCR to Show G. Spp. Occurrence in Sugar Beet.

A sample of 0.2 g of fresh tissue extracted sterilely from the interior of the hypocotyls was homogenized in 2 ml sterile water, and 1% PVPP was added to remove humic acid and to chelate Mg in the PCR. The homogenate was then filtered with 5 μm syringe filter and centrifuged at 13000 rpm for 10 min. The pellet was re-suspended in 200 ul water of which 1 ul was used for PCR.

The PCR for the detection of *G. diazotrophicus* was performed by genetic method based on 16S rRNA gene sequence with the species-specific primers AC (5'-CTGTTTCCCG-CAAGGGAC-3') (SEQ ID NO: 1) and DI (5'-GCGCCCCAT-TGCTGGGTT-3') (SEQ ID NO: 2). The species-specific PCR for *G. johannae* was performed with the universal primer U475 (5'-AATGACTGGGCGTAAAG-3') (SEQ ID NO: 3) and with one specific primer: L927Gj (5'-GAAAT-GAACATCTCTGCT-3') (SEQ ID NO: 4). (Fuentes-Ramires et al. 2001, Intl. J. Syst. Evol. Microbiol. 51:1305; Muthukumarasamy et al. 2005, Syst. Appl. Miocrobiol. 28:277).

The PCR was carried out using 1 uM of each primer, 10 ul of buffer, 1.25 mM dNTP and 1.5 mM MgCl2. 1 ul of sample. After a 10 min denaturation cycle at 95° C., 2 U of Taq-Polyemrase was added followed by 35 cycles of 95° C. for 1 min, 52° C. for 2 min, then 72° C. for 2 min, and final cycle at 72° C. for 10 min. PCR product was quantified using gel electrophoresis (1% agarose gel and TBE buffer) and with PCR analysis of pure cultures of *G. diazotrophicus* and *G. johannae* for controls.

Results

Choice of *Gluconacetobacter* spp. Strains

Nitrogenase activities of 30 strains were tested by acetylene reduction assay (ARA) with both semisolid LGI-P medium and semisolid LGI-P mixed with ground sugar beet hypocotyl tissue medium. Nitrogenase activity, the common indicator of $N_2$ fixation, can be assessed using a variety of techniques. The ARA test is based on the ability of the nitrogenase enzyme complex to reduce a variety of triple-bonded substrates, including acetylene, as analogs to $N_2$ gas. Nitrogenase reduces acetylene to ethylene versus $N_2$ to $NH_3$, in an approximate ratio of 3:1. This ratio varies, depending on the extent to which nitrogenase reduces $H_2$ from $H^+$, which occurs in parallel with N2 reduction to NH3. 14 strains with relative high AR activity were selected for inoculation (Table 1). One may optionally use any strain having AR activity, however typically one will use a strain having AR activity at least as high or higher than the strains in Table 1. Typically one assesses AR activity based upon peak height from gas chromotography for C2H4 production.

TABLE 1

Selection of 14 strains of *Gluconacetobacter* spp. for sugar beet inoculation

| Species | Strain | Source | Institution | Genetically engineered | Country of origin | Other designations/ culture listings | Reference |
|---|---|---|---|---|---|---|---|
| *G. diazotrophicus* | SRT4 LsdA− | Lazaro Hernandez | CGEB[1] | Under expression of levan sucrase A | Cuba | | Hernandez et al., 2000. Arch Microbiology, 172: 120-124 |

TABLE 1-continued

Selection of 14 strains of *Gluconacetobacter* spp. for sugar beet inoculation

| Species | Strain | Source | Institution | Genetically engineered | Country of origin | Other designations/ culture listings | Reference |
|---|---|---|---|---|---|---|---|
| *G. diazotrophicus* | SRT4 LsdB++ | Lazaro Hernandez | CGEB[1] | Over expression of levanase B | Cuba | | |
| *G. diazotrophicus* | CFNE 550 | Jesus Caballero-Mellado | UNAM[2] | | Mexico | | Caballero-Mellado et al. 1995. Appl. Environ. Microbiol. 61: 3008-3013. |
| *G. diazotrophicus* | PSP22 | | EMBRAPA[3] | | Brazil | | Caballero-Mellado et al. 1995. Appl. Environ. Microbiol. 61: 3008-3013. |
| *G. johannae* | UAP-CF51 | Jesus Caballero-Mellado | UNAM[2] | | Mexico | | Jimenez-Salgado et al. 1997. Appl. Environ. Microbiol. 63: 3676-3683. |
| *G. johannae* | CFN-CF52 | Jesus Caballero-Mellado | UNAM[2] | | Mexico | | Jimenez-Salgado et al. 1997. Appl. Environ. Microbiol. 63: 3676-3683. |
| *G. johannae* | CFN-CF76 | Jesus Caballero-Mellado | UNAM[2] | | Mexico | | Luis E. Fuentes-Ram!rez, et al. 2001. Intl. J. Syst. Evol. Micorbiol. 51: 1305-1314. |
| *G. diazotrophicus* | SRT4 | Lazaro Hernandez | CGEB[1] | | Cuba | | Coego A. et al. 1992. Rev Latamer Microbiol 34: 189-195 |
| *G. diazotrophicus* | PAL5T | | EMBRAPA[3] | | Brazil | PAI 5; PAL 5; ATCC 49037; CCUG 37298; CIP 103539; DSM 5601; LMG 7603; NCCB 89154 | Caballero-Mellado et al. 1994. Appl. Environ. Microbiol. 60: 1532-1537. |
| *G. diazotrophicus* | PAL5T LsdA− | Lazaro Hernandez | CGEB[1] | Underexpression of levan sucrase A | Cuba | | |
| *G. diazotrophicus* | PAL5T LsdB++ | Lazaro Hernandez | CGEB[1] | Overexpression of levanase B | Cuba | | |
| *G. diazotrophicus* | PAL5 | Lazaro Hernandez | CGEB[1] | | Cuba | PAI 5; PAL 5; ATCC 49037; CCUG 37298; CIP 103539; DSM 5601; LMG 7603; NCCB 89154 | Z. DONG, et al. 1995. Appl. Enviro. Microbiol. 61: 1843-1846. |
| *G. diazotrophicus* | PAL3 | | UNAM[2] | | Brazil | Pal 3; PAL 3; LMG 8066 | Caballero-Mellado et al. 1994. Appl. Environ. Microbiol. 60: 1532-1537. |
| *G. diazotrophicus* | UAP AC7 | Jesus Caballero-Mellado | UNAM[2] | | Mexico | | Tapia-Hernández A, et al. 2000. Microb Ecol 39: 49-55. |
| *G. diazotrophicus* | 1772 | Jesus Caballero-Mellado | UNAM[2] | | Australia | | Caballero-Mellado et al. 1995. Appl. Environ. Microbiol. 61: 3008-3013. |

TABLE 1-continued

Selection of 14 strains of *Gluconacetobacter* spp. for sugar beet inoculation

| Species | Strain | Source | Institution | Genetically engineered | Country of origin | Other designations/ culture listings | Reference |
|---|---|---|---|---|---|---|---|
| G. diazotrophicus | T2 | Lazaro Hernandez | CGEB[1] | | Cuba | | F. G. Loiret, et al. 2004. Journal of Applied Microbiology 2004, 97, 504-511 |

[1]Center for Genetic Engineering and Biotechnology, Havana, Cuba
[2]Universidad Nacional Autonoma de Mexico, Cuernavaca, Morelos, Mexico
[3]Empresa Brasileira de Pesquisa Agropecuária, Brazil
[4]Sugar Research Institute, Queensland, Australia
Strains containing the term LsdA− have been genetically engineered for the underexpression of levan sucrase A (lsdA) gene.
Strains containing the term LsdB++ have been genetically engineered for the overexpression of levanase B (lsdB) gene.

The methods described herein optionally comprise use of a *Gluconacetobacter* transfected with a levanase B (lsdB) gene (eg. DDBJ/EMBL/GenBank accession number L41732) to overexpress levanase B (lsdB) in the sucrose rich plant, typically sugar beet. In other embodiments, the methods comprise use of a *Gluconacetobacter* genetically engineered for the underexpression of levan sucrase A (lsdA) gene in the sucrose rich plant, typically sugar beet.

Post-Inoculation Sugar Beet Shoot Biomass Evaluation after 1 mM Nitrogen Treatment Biomass of shoots in sugar beet inoculated with different strains of G. spp. and treated with 1 mM nitrogen (N) for 12 weeks in sand culture. Each value is a mean of 5 replicates. Significance was compared only between control and each treatment. It was found that inoculation increased accumulation of biomass in all sugar beet tissues. In the shoots, the increment ranged from 3.3% to 57% as compared to uninoculated control in the treatment with 1 mM N (Table 2). Except strains of *G. diazotrophicus* SRT4 LsdA− and *G. diazotrophicus* T2, shoot biomass was significantly increased in the plants inoculated with other strains.

TABLE 2

| *Gluconacetobacter* spp. | Shoots Dry weight (mg) | S.E. | Signif. α = 0.05 | % increase comp. with cont. |
|---|---|---|---|---|
| Control(uninoculated) | 1800.4 | 181.8 | a | 0.0 |
| G. d. SRT4 LsdA− | 2134.8 | 89.2 | a | 18.6 |
| G. d. SRT4 LsdB++ | 2441.2 | 104.8 | b | 35.6 |
| G. d. CFNE 550 | 2378.0 | 174.9 | b | 32.1 |
| G. d. PSP 22 | 2532.8 | 151.6 | b | 40.7 |
| G. j. UAP-Cf 51 | 2439.6 | 223.0 | b | 35.5 |
| G. j. CFN-Cf 52 | 2568.8 | 117.3 | b | 42.7 |
| G. j. CFN-cf 76 | 2488.4 | 121.4 | b | 38.2 |
| G. d. SRT4 | 2381.4 | 184.3 | b | 32.3 |
| G. d. PAL5T | 2677.4 | 129.5 | b | 48.7 |
| G. d. PAL5T LsdA− | 2415.0 | 175.3 | b | 34.1 |
| G. d. PAL5T LsdB++ | 2589.2 | 170.9 | b | 43.8 |
| G. d. UAP AC7 | 2827.4 | 282.8 | b | 57.0 |
| G. d. 1772 | 2604.6 | 93.8 | b | 44.7 |
| G. d. T2 | 1859.8 | 150.5 | a | 3.3 |

Treatments listed with different levels of significance (a or b) are statistically different from each other with α=0.05.

Post-Inoculation Sugar Beet Root Biomass Evaluation after 1 mM Nitrogen Treatment For the purposes of this application, the term "root" is being used to refer to the fibrous roots subtending the commercially harvestable "beet" portion of the sugar beet plant. Biomass of roots in sugar beet inoculated with different strains of G. spp. and treated with 1 mM N for 12 weeks in sand culture. Each value is a mean of 5 replicates. Significance was compared only between control and each treatment. Improvement of biomass accumulation occurred in roots inoculated with all strains. The increment ranged from 16.1% to 59.3% and reached significant levels, at least, in 7 strains (Table 3).

TABLE 3

| *Gluconacetobacter* spp. | Roots Dry weight (mg) | S.E. | Signif. α = 0.05 | % increase comp. with cont. |
|---|---|---|---|---|
| Control(uninoculated) | 571.4 | 81.3 | a | 0.0 |
| G. d. SRT4 LsdA− | 663.2 | 71.1 | a | 16.1 |
| G. d. SRT4 LsdB++ | 703.8 | 95.4 | a | 23.2 |
| G. d. CFNE 550 | 827.8 | 72.6 | b | 44.9 |
| G. d. PSP 22 | 792.8 | 81.2 | b | 38.7 |
| G. j. UAP-Cf 51 | 691.8 | 46.4 | a | 21.1 |
| G. j. CFN-Cf 52 | 777.4 | 120.5 | a | 36.1 |
| G. j. CFN-cf 76 | 912.0 | 45.5 | b | 59.6 |
| G. d. SRT4 | 727.0 | 118.6 | a | 27.2 |
| G. d. PAL5T | 910.2 | 108.3 | b | 59.3 |
| G. d. PAL5T LsdA− | 787.8 | 62.2 | b | 37.9 |
| G. d. PAL5T LsdB++ | 878.2 | 35.3 | b | 53.7 |
| G. d. UAP AC7 | 765.4 | 90.5 | a | 34.0 |
| G. d. 1772 | 856.8 | 44.7 | b | 49.9 |
| G. d. T2 | 685.0 | 120.7 | a | 19.9 |

Treatments listed with different levels of significance (a or b) are statistically different from each other with α=0.05.

Post-Inoculation Sugar Beet Hypocotyls Biomass Evaluation after 1 mM Nitrogen Treatment The term "hypocotyl" is being used herein to refer to the commercially harvestable "beet" portion of the sugar beet plant (following Artschwager's terminology that the sugar beet hypocotyls represent the broadest part of the "beet" (Artschwager, E. 1926. J Agr Res 33:143), but recognizing that the "beet" portion of a sugar beet (ie. "sugar beet" refers to the entire plant herein) anatomically consists of hypocotyls and part of the root of the plant. Biomass of hypocotyls in sugar beet inoculated with different strains of G. spp. and treated with 1 mM N for 12 weeks in sand culture. Each value is a mean of 5 replicates. Significance was compared only between control and each treatment. It was noticed that the largest increase in biomass occurred in hypocotyl tissues. This is a significant advantage of the invention in that the hypocotyls tissue is the most commercially important part of the plant. The strain of G. d. PAL5T LsdB++ appeared a highest improvement for hypocotyl growth. The increment reached 110.6% compared with control (Table 4).

TABLE 4

| Gluconacetobacter spp. | Hypocotyls Dry weight (mg) | S.E. | Signif. α = 0.05 | % increase comp. with cont. |
|---|---|---|---|---|
| Control(uninoculated) | 1826.4 | 306.0 | a | 0.0 |
| G. d. SRT4 LsdA− | 2266.2 | 300.1 | a | 24.1 |
| G. d. SRT4 LsdB++ | 3129.6 | 481.2 | b | 71.4 |
| G. d. CFNE 550 | 2504.6 | 377.9 | a | 37.1 |
| G. d. PSP 22 | 2295.8 | 77.1 | a | 25.7 |
| G. j. UAP-Cf 51 | 3279.0 | 417.5 | b | 79.5 |
| G. j. CFN-Cf 52 | 2183.4 | 267.5 | a | 19.5 |
| G. j. CFN-cf 76 | 2731.6 | 501.7 | a | 49.6 |
| G. d. SRT4 | 3247.2 | 363.7 | b | 77.8 |
| G. d. PAL5T | 2731.8 | 322.2 | a | 49.6 |
| G. d. PAL5T LsdA− | 3093.4 | 398.6 | b | 69.4 |
| G. d. PAL5T LsdB++ | 3847.0 | 545.9 | b | 110.6 |
| G. d. UAP AC7 | 2500.0 | 328.3 | a | 36.9 |
| G. d. 1772 | 3087.8 | 227.1 | b | 69.1 |
| G. d. T2 | 1754.6 | 231.7 | a | −3.9 |

Treatments listed with different levels of significance (a or b) are statistically different from each other with α=0.05.

Post-Inoculation Sugar Beet Shoot Biomass Evaluation after 10 mM Nitrogen Treatment Biomass of shoots in sugar beet inoculated with different strains of G. spp. and treated with 10 mM N for 12 weeks in sand culture. Each value is a mean of 5 replicates. Significance was compared only between control and each treatment. By comparison of the increments between the treatment with 1 mM N and 10 mM N, it is clear that improvement of sugar beet growth was much lower in the treatments with 10 mM N than with 1 mM N. Most of strains did not show a significant effect on shoot biomass accumulation; only G. d. PAL5T increased to a significant level (27.2% increase) (Table 5).

TABLE 5

| Gluconacetobacter spp. | Shoots Dry weight (mg) | S.E. | Signif. α = 0.05 | % increase comp. with cont. |
|---|---|---|---|---|
| Control (uninoculated) | 13532.4 | 959.2 | a | 0.0 |
| G. d. SRT4 LsdA− | 13760.6 | 731.3 | a | 1.7 |
| G. d. SRT4 LsdB++ | 13895.4 | 978.0 | a | 2.7 |
| G. d. CFNE 550 | 13635.4 | 1480.1 | a | 0.8 |
| G. d. PSP 22 | 14991.4 | 873.3 | a | 10.8 |
| G. j. UAP-Cf 51 | 12534.4 | 1810.9 | a | −7.4 |
| G. j. CFN-Cf 52 | 14373.6 | 1204.8 | a | 6.2 |
| G. j. CFN-cf 76 | 14441.0 | 866.3 | a | 6.7 |
| G. d. SRT4 | 14032.3 | 1033.1 | a | 3.7 |
| G. d. PAL5T | 17215.4 | 1543.8 | b | 27.2 |
| G. d. PAL5T LsdA− | 14731.4 | 766.8 | a | 8.9 |
| G. d. PAL5T LsdB++ | 13353.4 | 672.6 | a | −1.3 |
| G. d. UAP AC7 | 14725.0 | 1736.2 | a | 8.8 |
| G. d. 1772 | 13641.4 | 374.7 | a | 0.8 |
| G. d. T2 | 12728.0 | 956.4 | a | −5.9 |

Treatments listed with different levels of significance (a or b) are statistically different from each other with α=0.05.

Post-Inoculation Sugar Beet Root Biomass Evaluation after 10 mM Nitrogen Treatment Biomass of roots in sugar beet inoculated with different strains of G. spp. and treated with 10 mM N for 12 weeks in sand culture. Each value is a mean of 5 replicates. Significance was compared only between control and each treatment. Significance was compared only between control and each treatment. In roots, all strains showed positive improvement (Table 6) and 4 strains increased biomass accumulations to significant levels.

TABLE 6

| Gluconacetobacter spp. | Roots Dry weight (mg) | S.E. | Signif. α = 0.05 | % increase comp. with cont. |
|---|---|---|---|---|
| Control(uninoculated) | 3359.2 | 336.8 | a | 0.0 |
| G. d. SRT4 LsdA− | 5439.6 | 1241.3 | b | 61.9 |
| G. d. SRT4 LsdB++ | 3958.8 | 515.3 | a | 17.8 |
| G. d. CFNE 550 | 4448.2 | 344.1 | a | 32.4 |
| G. d. PSP 22 | 4457.4 | 593.6 | a | 32.7 |
| G. j. UAP-Cf 51 | 4164.0 | 616.9 | a | 24.0 |
| G. j. CFN-Cf 52 | 4065.8 | 233.5 | a | 21.0 |
| G. j. CFN-cf 76 | 4432.0 | 652.1 | a | 31.9 |
| G. d. SRT4 | 4724.4 | 345.0 | a | 40.6 |
| G. d. PAL5T | 5487.8 | 534.0 | b | 63.4 |
| G. d. PAL5T LsdA− | 5130.0 | 599.6 | b | 52.7 |
| G. d. PAL5T LsdB++ | 5896.4 | 802.3 | b | 75.5 |
| G. d. UAP AC7 | 4643.2 | 666.8 | a | 38.2 |
| G. d. 1772 | 4493.2 | 233.2 | a | 33.8 |
| G. d. T2 | 4670.8 | 709.8 | a | 39.0 |

Treatments listed with different levels of significance (a or b) are statistically different from each other with α=0.05.

Post-Inoculation Sugar Beet Hypocotyls Biomass Evaluation after 10 mM Nitrogen Treatment Biomass of hypocotyls in sugar beet inoculated with different strains of G. spp. and treated with 10 mM N for 12 weeks in sand culture. Each value is a mean of 5 replicates. Significance was compared only between control and each treatment. More significant improvement was also found in hypocotyl tissues in the beets treated with 10 mM N. However, the range of improvement was less in the treatment with 10 mM N (Table 7) than with 1 mM N (Table 4).

TABLE 7

| Gluconacetobacter spp. | Hypocotyls Dry weight (mg) | S.E. | Signif. α = 0.05 | % increase comp. with cont. |
|---|---|---|---|---|
| Control(uninoculated) | 15943.2 | 2338.1 | a | 0.0 |
| G. d. SRT4 LsdA− | 21461.2 | 1583.9 | b | 34.6 |
| G. d. SRT4 LsdB++ | 23352.6 | 280.4 | b | 46.5 |
| G. d. CFNE 550 | 20880.4 | 930.3 | a | 31.0 |
| G. d. PSP 22 | 22376.8 | 1445.0 | b | 40.4 |
| G. j. UAP-Cf 51 | 21183.6 | 3500.1 | a | 32.9 |
| G. j. CFN-Cf 52 | 21952.2 | 2438.0 | b | 37.7 |
| G. j. CFN-cf 76 | 26035.4 | 1391.2 | b | 63.3 |
| G. d. SRT4 | 26671.4 | 1969.1 | b | 67.3 |
| G. d. PAL5T | 22711.4 | 1879.3 | b | 42.5 |
| G. d. PAL5T LsdA− | 19984.0 | 1789.2 | a | 25.3 |
| G. d. PAL5T LsdB++ | 22736.4 | 3825.9 | b | 42.6 |
| G. d. UAP AC7 | 24248.6 | 2652.4 | b | 52.1 |
| G. d. 1772 | 21317.0 | 1916.7 | a | 33.7 |
| G. d. T2 | 22099.6 | 1959.4 | b | 38.6 |

Treatments listed with different levels of significance (a or b) are statistically different from each other with α=0.05.

Post-Inoculation Nitrogen Fixation Rates in Sugar Beets

In Table 8, nitrogen fixation rate in sugar beet inoculated with different strains of G. spp. and treated with 1 mM N for 12 weeks in sand culture. Each value is a mean of 5 replicates. In Table 9, nitrogen fixation rate in sugar beet inoculated with different strains of G. spp. and treated with 10 mM N for 12 weeks in sand culture. Each value is a mean of 5 replicates. The improvement of biomass accumulation by inoculation with 14 strains of G. spp. in all beet tissues was well matched with corresponding nitrogen fixation rate in both treatments with 1 and 10 mM N. Nitrogen fixation rate was higher in treatment with 1 mM N than in 10 mM N (Tables 8 and 9). The highest nitrogen fixation rate was found in the roots inoculated with G. d. PAL5T LsdB++ and 24.4% of N was derived from nitrogen fixation (Table 8). It is interesting that nitrogen fixation rate was increased from shoot, hypocotyl to root in both treatments and all inoculations (Tables 8 and 9).

TABLE 8

| Gluconacetobacter Spp. | Nitrogen fixation rate (% of N derived from atmosphere) | | | | | |
|---|---|---|---|---|---|---|
| | Shoots | S.E. | Hypo-cotyls | S.E. | Roots | S.E. |
| Control(uninoculated) | 0.0 | 0.0 | 0.0 | 0.0 | 0.0 | 0.0 |
| G. d. SRT4 LsdA− | 9.5 | 2.7 | 10.8 | 2.4 | 15.3 | 3.8 |
| G. d. SRT4 LsdB++ | 11.7 | 3.1 | 12.4 | 2.5 | 16.9 | 3.3 |
| G. d. CFNE 550 | 10.1 | 2.4 | 9.9 | 1.5 | 13.9 | 2.2 |
| G. d. PSP 22 | 10.0 | 0.9 | 11.0 | 0.7 | 15.5 | 0.7 |
| G. j. UAP-Cf 51 | 9.1 | 1.4 | 12.1 | 1.6 | 15.0 | 1.9 |
| G. j. CFN-Cf 52 | 10.5 | 0.7 | 11.7 | 0.8 | 16.2 | 1.6 |
| G. j. CFN-cf 76 | 12.8 | 1.2 | 13.6 | 1.4 | 18.1 | 1.7 |
| G. d. SRT4 | 12.1 | 2.5 | 14.3 | 2.3 | 18.7 | 2.5 |
| G. d. PAL5T | 15.8 | 1.2 | 16.8 | 1.1 | 21.9 | 1.4 |
| G. d. PAL5T LsdA− | 13.8 | 2.0 | 13.7 | 3.2 | 21.4 | 1.9 |
| G. d. PAL5T LsdB++ | 17.9 | 1.8 | 18.6 | 2.1 | 24.6 | 2.7 |
| G. d. UAP AC7 | 16.0 | 2.6 | 17.4 | 2.6 | 21.7 | 1.9 |
| G. d. 1772 | 15.6 | 1.0 | 17.2 | 0.4 | 22.6 | 1.2 |
| G. d. T2 | 8.3 | 1.7 | 9.8 | 2.0 | 14.7 | 2.4 |

TABLE 9

| Gluconacetobacter Spp. | Nitrogen fixation rate (% of N derived from atmosphere) | | | | | |
|---|---|---|---|---|---|---|
| | Shoots | S.E. | Hypo-cotyls | S.E. | Roots | S.E. |
| Control(uninoculated) | 0.0 | 0.0 | 0.0 | 0.0 | 0.0 | 0.0 |
| G. d. SRT4 LsdA− | 0.0 | 0.6 | 1.6 | 0.8 | 3.4 | 1.2 |
| G. d. SRT4 LsdB++ | 0.0 | 0.6 | 1.0 | 0.7 | 3.2 | 1.4 |
| G. d. CFNE 550 | 0.0 | 0.4 | 0.8 | 0.4 | 3.1 | 0.9 |
| G. d. PSP 22 | 0.0 | 0.6 | 1.4 | 1.0 | 3.5 | 0.9 |
| G. j. UAP-Cf 51 | 0.0 | 0.9 | 1.1 | 1.1 | 4.6 | 1.9 |
| G. j. CFN-Cf 52 | 0.0 | 0.9 | 1.4 | 1.4 | 4.9 | 1.6 |
| G. j. CFN-cf 76 | 0.2 | 0.9 | 2.3 | 0.8 | 3.1 | 1.4 |
| G. d. SRT4 | 0.4 | 0.7 | 2.2 | 0.6 | 3.1 | 1.5 |
| G. d. PAL5T | 0.0 | 0.5 | 1.4 | 0.6 | 3.6 | 1.2 |
| G. d. PAL5T LsdA− | 0.0 | 0.6 | 2.3 | 1.4 | 4.5 | 1.3 |
| G. d. PAL5T LsdB++ | 0.0 | 0.4 | 1.6 | 0.6 | 3.9 | 0.9 |
| G. d. UAP AC7 | 0.5 | 0.4 | 2.7 | 0.8 | 5.0 | 0.7 |
| G. d. 1772 | 0.0 | 0.7 | 1.5 | 0.6 | 3.2 | 1.0 |
| G. d. T2 | 0.0 | 0.7 | 1.5 | 0.6 | 4.6 | 1.2 |

Nitrogen fixation in non-vegetables has been reported in a variety of plant species. This kind of N-fixing ability is often attributed to endophytic diazotrophs, such as *Gluconacetobacter*. Endophytic diazotrophs isolated from their hosts and introduced into non-host species to improve plant growth have been previously reported. However, commercially significant increase in sugar beet production by introducing endophytic diazotrophs has not been reported. It is demonstrated here that all 14 strains of G. spp. improved sugar beet growth to different extents. These effects were well associated with N-fixing activity in these tissues.

The PCR was carried out on samples of hypocotyl tissue from each inoculation treatment and from uninoculated plants. PCR product corresponding to PCR product bands from pure cultures of *G. johannae* and *G. diazotrophicus* were obtained on many extracts from sugar beets inoculated with strains *G. johannae* UAP-Cf51, *G. johannae* CFN-Cf52 and *G. johannae* CFN-Cf76, and with strains *G. diazotrophicus* PAL5T LsdB++ and *G. diazotrophicus* 1772. No PCR product was produced from extracts from uninoculated sugar beets. These results show that the bacterium is colonizing the interior of the hypocotyls (i.e. beets). It is very significant that the bacterium is in the interior of the plant. It is a major breakthrough" of the present invention to demonstrate that inoculation with *Glucoacetobacter* results in the plant colonizing the interior of the plant, not just the surface of the root (as in epiphytes) or the soil around the root (the "rhizosphere" of the roots). Since the bacterium is in the hypocotyls, it is expected to be present in shoot and root as well.

In comparing the data contained in Tables 2-7 it is notable that although inoculation with *Gluconacetobacter* sp. resulted in the stimulation of growth in all plant parts (i.e. shoots, root, hypocotyls) by some strains, the highest improvement of sugar beet production was in hypocotyl (beet) tissues (Tables 4 and 7), with a maximum stimulation of 110.6% (Table 4) as compared to the uninoculated control. In contrast, the lowest proportional enhancement among plant parts from inoculation was in shoots (Table 2 and 5). Stimulation of root growth for plants grown at the 1 mM and 10 mM level of $NO_3^-$ supply showed improvements for every strain of bacteria (Table 3 and 6). Without wishing to be bound by theory, the greater performance by the *Gluconacetobacter* sp. strains in hypocotyls (beets) than in shoots may be related with the fact that the hypocotyls (beets) had a much greater concentration of sucrose (17.3% of fresh weight (FW)) as compared to shoots (0.16% FW). *G. diazotrophicus* grows and fixes $N_2$ much better in solid medium containing sucrose than other sugar sources (i.e. glucose and fructose) (Vessey and Pan, 2003, Symbiosis 35: 181).

The data in Tables 2-7 also show that the enhancement of growth of plant parts (shoot, root, hypocotyl) by inoculation with *Gluconacetobacter* sp. varied with strain. However, it is notable that across all plant parts, and the two levels of N (1 and 10 mM $NO_3^-$) supplied to the plants, the genetically engineered strain, *G. diazotrophicus* PAL5T LsdB++ consistently lead to some of the highest enhancements of growth (except for shoots at 10 mM N; Table 2). The LsdB++ transformation results in an overexpression of the exo-levanase B (lsdB) gene (DDBJ/EMBL/GenBank accession number L41732; see Menedez et al. 2002, Current Microbiology 45: 5-12). Therefore, an aspect of this invention relates to methods of using *Gluconacetobacter* sp. transformed with this gene for increasing plant biomass by colonizing the plants with the *Gluconacetobacter* sp. Among the non-genetically engineered strains, *G. diazotrophicus* PAL5T was the most consistent in significantly enhancing growth of the plant parts. Good results were also obtained with some strains (lsdA−) that have been genetically engineered to under-express the levansucrase A (lsdA) gene (Arrieta et al. 1996, Microbiology-UK 142: 1077; Batista et al. 1999, Biochem J. 337: 503). The lsdA gene codes for levansucrase (EC 2.4.1.10) and it sequence is also available under the GSDB accession number L41732.

In comparing the data in Table 8 to those in Table 9, it is notable that $N_2$ fixation within plant parts was much greater due to inoculation with *Gluconacetobacter* sp. at 1 mM than at 10 mM $NO_3^-$. This may be related to the fact that there is evidence that *G. diazotrophicus* fixes more $N_2$ at lower levels of $NO_3^-$ or $NH_4^+$ in solid medium culture (Vessey and Pan, 2003, Symbiosis 35: 181). Therefore, these data and observations show that greater relative growth promotion in sugar beet plants supplied at the lower level of N (1 mM; Table 2, 3, 4) compared to the higher level of N (10 mM Table 5, 6, 7) due to the inoculation with *Glucoacetobacter* strains is related, at least in part, to N2 fixation by the bacterium.

Despite the low levels of $N_2$ fixation in inoculated sugar beet plants grown at 10 mM $NO_3^-$ (Table 9), it is notable that there were still many instances of enhanced growth of roots (Table 6) and hypocotyls (beets) (Table 7) for plants supplied with 10 mM $NO_3^-$. Without wishing to be bound by theory, there appear to be other factors causing the stimulation of growth in sugar beet from inoculation with *Gluconacetobacter* sp. These other factors include the production of phytohormones. There is evidence that *G. diazotrophicus* produces the phytohormone indole-3-acetic acid (IAA) (Fuentes-Ramirez et al. 1993, Plant Soil 154:145; Madhaiyan et al. 2004, Microbiol Res 159:233) and gibberellins (GA) (Bastian et al. 1998; Plant Growth Regul 24:7) and that these hormones may be involved in the growth promotion by the bacterium in sugarcane (de Matos Nogueira et al. 2001, Genet Mol Biol 24:199). Therefore, the present invention for the first time demonstrates that *Gluconacetobacter* sp. provides increased nitrogen fixation and increased production of other compounds that dramatically increase plant biomass.

The above data indicates that inoculation of sugar beet with certain strains of *Gluconacetobacter* sp. increases sucrose-rich crop, such as sugar beet, usefulness as biofuel feedstocks (eg. ethanol), not only in increased biomass accumulation but also in reduction of N fertilizer use (Demirbas, 2009, Energy Sources, Part A: 31:1573-1582).

Sucrose rich plants, such as sugar beet, have many commercial uses. The yield/per hectare for sugar beet can be ten times greater than other grain crops and the energy requirements for processing sugar are less. The present invention will have important implications that significantly impact on cost competitiveness of sugar beet production in temperate regions. The present invention is readily applied in the alternative energy sector to provide feedstock production for the biofuel industry in temperate regions across the globe (explained in more detail below). From a biological perspective, sugar beet is considered the best crop for producing sugar-to-ethanol in temperate regions partly because of its high yield and sugar content. The plants of the invention are also useful in food production i.e to produce refined white or brown sugar used in food and baked products such as cereals/breads. The plants are also useful as livestock feed eg. sugar beet pulp and tops (protein, vitamin A) is useful as supplement for sheep and cattle ranchers Sucrose-rich crops, such as sugar beets, are useful in methods of producing biofuel, such as ethanol, through an ethanol fermentation process. This method typically involves fermenting a sucrose-rich plant by contacting the plant (typically a homogenized portion of the plant, such as a portion of a sugar beet such as a sugar beet hypocotyl) in a fermentation medium that comprises yeast, under conditions suitable for fermentation. Sugars such as glucose, fructose, and sucrose are converted into cellular energy and thereby produce ethanol and carbon dioxide as metabolic waste products. The end product, after distillation of the fermentation medium, is ethanol, typically at a concentration of at least 80% or 90% ethanol and optionally up to 96% or 99% ethanol. Since yeasts perform this process in the absence of oxygen, ethanol fermentation is classified as anaerobic. This method provides an ethanol product which is cheap, clean and renewable.

The present invention will be more readily understood by referring to the following examples which are given to illustrate the invention rather than to limit its scope.

Example 1

LGI-P Liquid Medium for the *Gluconacetobacter* Composition pH 5.5 with 1% Acetic Acid

| | |
|---|---|
| $K_2HPO_4$ | 0.2 g/L |
| $KH_2PO_4$ | 0.6 g/L |
| $MgSO_4 \cdot 7H_2O$ | 0.2 g/L |
| $CaCl_2 \cdot 2H_2O$ | 0.02 g/L |
| $NaMoO_4 \cdot 2H_2O$ | 0.002 g/L |
| $FeCl_3 \cdot 6H_2O$ | 0.01 g/L |
| 0.5% bromothymol blue solution in 0.2M KOH | 5 ml/L |
| Biotin | 0.1 mg/L |
| Pyridoxal HCl | 0.2 mg/L |
| Sucrose | 100 g/L |
| $(NH_4)_2SO_4$ | 1.32 g/L |

Results from Experiments with Sugar Beet Growing in a Natural Soil.

All of the above results were obtained from experiments in which sugar beets were grown in pots containing sand as the rooting medium. The following experiments were conducted with sugar beet growing in a natural soil. In general, evidence of stimulation of plant growth due to inoculation of a potential plant-growth promoting bacterium is more difficult in natural soil than in sand, because the natural soil is a much more complex rooting medium and the bacterium in the inoculant has to compete against millions of other naturally occurring bacteria in the soil.

Material and Methods

Seeds of sugar beet (*Beta vulgaris* variety-Beta 5833R) were sown in plastic pots containing 3 kg sandy loam soil (obtained from the Annapolis Valley, Nova Scotia). This soils was a sandy loam (68% sand, 23.4% silt and 8.6% clay) with a pH of 6.9 (soil:water ratio 1:2) and had available nutrients in soil of: 14 ppm N, >60 ppm P, 106 ppm K, 3 ppm S, 55.4 ppm Fe, 1200 ppm Ca, 236 ppm Mg, 24.7 ppm Cu and 5.5 ppm Zn. The pots were placed in a greenhouse in which temperature was set to a minimum of 25/18° C. (day/night), and with supplemental lighting maintained to a minimum photoperiod of 16 h/8 h light/dark. The young seedlings were inoculated 18 days after planting (cotyledon leaves fully emerged; true leaves not yet emerged) with 11 stains of *G. diazotrophicus* and 3 strains of *G. johannae* by applying 1 ml of each bacterial broth (OD value at 600 nm=0.5; $10^7$ to $10^8$ colony forming units (CFU)/ml) to the surface of the soil around the base of each stem of the seedlings. The control plants were not inoculated. All inoculated plants were treated with 2 mM $NO_3^-$ or 10 mM $NO_3^-$ respectively. There were 8 replicates in each treatment. The plants were watered with 100 ml of water daily and fertilized with 100 ml of 2 mM $NO_3^-$ or 10 mM $NO_3^-$ modified Knop's nutrition solution twice a week (see composition below). After one month of growth, the plants were watered with 200 ml water daily, after two months, with 300 ml of water. The plants were harvested after 4 months of growth. Shoots and beets (no fiberous roots) were dried separately at 80° C. in oven.

Composition of Nutrient Solution Supplied to Sugar Beets Grown in a Natural Soil:

| | |
|---|---|
| Ca(NO$_3$)$_2$ | 0.656 g/L |
| KNO$_3$ | 0.202 g/L for 2 mM or 2.02 g/L for 10 mM |
| KH$_2$PO$_4$ | 0.250 g/L |
| MgSO$_4$ | 0.120 g/L |
| H$_3$BO$_3$ | 2.86 mg/L |
| MnCl$_2$•4H$_2$O | 1.81 mg/L |
| ZnSO$_4$•7H$_2$O | 0.22 mg/L |
| CuSO$_4$•5H$_2$O | 0.08 mg/L |
| H$_2$MoO$_4$•H$_2$O | 0.02 mg/L |
| FeSO$_4$•H$_2$O | 6.95 mg/L |

Nutrient solution was adjusted to a pH of 6.0

TABLE 10

Dry weight (DW) of shoots of sugar beet plants supplied with 2 mM NO$_3^-$ with no or different strains of G. diazotrophicus (G. d.) or G. johannae (G. j.).

| | Shoot | | % increase compared to | Signif. |
|---|---|---|---|---|
| Strain | DW (mg) | S.E. | control | α = 0.05 |
| No inoculation | 5151.1 | 240.8 | 0.0 | a |
| G. d. SRT4 LsdA− | 6182.4 | 285.2 | 20.0 | b |
| G. d. SRT4 LsdB++ | 5835.1 | 385.6 | 13.3 | a |
| G. d. CFNE 550 | 6456.3 | 339.8 | 25.3 | b |
| G. d. PSP 22 | 5730.5 | 557.2 | 11.2 | a |
| G. j. UAP-Cf 51 | 5688.4 | 348.1 | 10.4 | a |
| G. j. CFN-Cf 52 | 5309.9 | 604.5 | 3.1 | a |
| G. j. CFN-cf 76 | 6466.9 | 317.0 | 25.5 | b |
| G. d. SRT4 | 5796.4 | 286.5 | 12.5 | a |
| G. d. PAL5T | 6336.9 | 404.5 | 23.0 | b |
| G. d. PAL5T LsdA− | 6401.9 | 266.6 | 24.3 | b |
| G. d. PAL5T LsdB++ | 6385.3 | 148.5 | 24.0 | b |
| G. d. UAP AC7 | 6229.3 | 215.4 | 20.9 | b |
| G. d. 1772 | 6942.0 | 382.4 | 34.8 | b |
| G. d. T2 | 7108.4 | 38.0 | 38.0 | b |

Treatments listed with different levels of significance (a or b) are statistically different from each other with α=0.05.

Inoculation resulted in increases in shoot weight in all of the strains compared to the control treatment (10 strains showing statistical significance). The greatest increase was achieved with G. diazotrophicus T2 (38%). Averaged across all strains, the mean increase in shoot growth due to inoculation was 20.5%.

TABLE 11

Dry weight (DW) of beets (minus subtending fibrous roots) of sugar beet plants supplied with 2 mM NO$_3^-$ with no or different strains of G. diazotrophicus (G. d.) or G. johannae (G. j.).

| | Beet | | % increase compared to | Signif. |
|---|---|---|---|---|
| Strain | DW (mg) | S.E. | control | α = 0.05 |
| No inoculation | 13684.9 | 1212.2 | 0.0 | a |
| G. d. SRT4 LsdA− | 15428.9 | 1069.6 | 12.7 | a |
| G. d. SRT4 LsdB++ | 11225.5 | 1219.1 | −18.0 | a |
| G. d. CFNE 550 | 13218.5 | 914.8 | −3.4 | a |
| G. d. PSP 22 | 12365.5 | 984.1 | −9.6 | a |
| G. j. UAP-Cf 51 | 17103.9 | 1234.8 | 25.0 | b |
| G. j. CFN-Cf 52 | 13394.5 | 1489.2 | −2.1 | a |
| G. j. CFN-cf 76 | 17489.6 | 1304.4 | 27.8 | b |
| G. d. SRT4 | 15548.1 | 1073.9 | 13.6 | a |
| G. d. PAL5T | 17213.0 | 1743.6 | 25.8 | b |
| G. d. PAL5T LsdA− | 15397.8 | 398.6 | 12.5 | a |

TABLE 11-continued

Dry weight (DW) of beets (minus subtending fibrous roots) of sugar beet plants supplied with 2 mM NO$_3^-$ with no or different strains of G. diazotrophicus (G. d.) or G. johannae (G. j.).

| | Beet | | % increase compared to | Signif. |
|---|---|---|---|---|
| Strain | DW (mg) | S.E. | control | α = 0.05 |
| G. d. PAL5T LsdB++ | 19330.3 | 656.6 | 41.3 | b |
| G. d. UAP AC7 | 15910.4 | 745.4 | 16.3 | a |
| G. d. 1772 | 17119.4 | 1106.4 | 25.1 | b |
| G. d. T2 | 16544.4 | 1216.2 | 20.9 | a |

Treatments listed with different levels of significance (a or b) are statistically different from each other with α=0.05.

Inoculation resulted in increases in beet weight in 10 of the 14 strains compared to the control treatment. The greatest increase was achieved with G. diazotrophicus PAL5T LsdB++ (41.3%). Averaged across all strains, the mean increase in beet growth due to inoculation was 13.4%.

TABLE 12

Dry weight (DW) of shoots of sugar beet plants supplied with 10 mM NO$_3^-$ with no or different strains of G. diazotrophicus (G. d.) or G. johannae (G. j.).

| | Shoot | | % increase compared to | Signif. |
|---|---|---|---|---|
| Strain | DW (mg) | S.E. | control | α = 0.05 |
| No inoculation | 25343.3 | 1008.8 | 0.0 | a |
| G. d. SRT4 LsdA− | 23484.5 | 1167.6 | −7.3 | a |
| G. d. SRT4 LsdB++ | 22841.0 | 1403.7 | −9.9 | a |
| G. d. CFNE 550 | 23848.6 | 979.3 | −5.9 | a |
| G. d. PSP 22 | 22546.5 | 881.4 | −11.0 | a |
| G. j. UAP-Cf 51 | 23317.9 | 1200.1 | −8.0 | a |
| G. j. CFN-Cf 52 | 23941.1 | 1468.7 | −5.5 | a |
| G. j. CFN-cf 76 | 24311.9 | 787.9 | −4.1 | a |
| G. d. SRT4 | 25441.8 | 1658.5 | 0.4 | b |
| G. d. PAL5T | 22096.9 | 928.9 | −12.8 | b |
| G. d. PAL5T LsdA− | 22982.6 | 1688.4 | −9.3 | a |
| G. d. PAL5T LsdB++ | 22722.9 | 817.7 | −10.3 | a |
| G. d. UAP AC7 | 23001.6 | 828.3 | −9.2 | a |
| G. d. 1772 | 22430.5 | 963.4 | −11.5 | a |
| G. d. T2 | 22555.1 | 751.9 | −11.0 | a |

Treatments listed with different levels of significance (a or b) are statistically different from each other with α=0.05.

None of the 14 strains tested resulted in increases in shoot weight in sugar beet plants supplied with 10 mM NO$_3^-$ compared to the control treatment.

TABLE 13

Dry weight (DW) of beets (minus subtending fibrous roots) of sugar beet plants supplied with 10 mM NO$_3^-$ with no or different strains of G. diazotrophicus (G. d.) or G. johannae (G. j.).

| | Beet | | % increase compared to | Signif. |
|---|---|---|---|---|
| Strain | DW (mg) | S.E. | control | α = 0.05 |
| No inoculation | 33281.1 | 2745.2 | 0.0 | a |
| G. d. SRT4 LsdA− | 35824.8 | 2684.8 | 7.6 | a |
| G. d. SRT4 LsdB++ | 35164.8 | 3347.2 | 5.7 | a |
| G. d. CFNE 550 | 36270.3 | 2714.2 | 9.0 | a |

TABLE 13-continued

Dry weight (DW) of beets (minus subtending fibrous roots) of sugar beet plants supplied with 10 mM $NO_3^-$ with no or different strains of G. diazotrophicus (G. d.) or G. johannae (G. j.).

| Strain | Beet DW (mg) | S.E. | % increase compared to control | Signif. $\alpha = 0.05$ |
|---|---|---|---|---|
| G. d. PSP 22 | 32338.3 | 3900.3 | −2.8 | a |
| G. j. UAP-Cf 51 | 38659.4 | 1827.3 | 16.2 | a |
| G. j. CFN-Cf 52 | 32265.5 | 3050.6 | −3.1 | a |
| G. j. CFN-cf 76 | 39016.1 | 1972.3 | 17.2 | a |
| G. d. SRT4 | 34640.8 | 2621.6 | 4.1 | a |
| G. d. PAL5T | 38457.8 | 2610.1 | 15.6 | a |
| G. d. PAL5T LsdA− | 37318.4 | 2530.5 | 12.1 | a |
| G. d. PAL5T LsdB++ | 41419.9 | 2918.3 | 24.5 | b |
| G. d. UAP AC7 | 41638.6 | 2386.1 | 25.1 | b |
| G. d. 1772 | 34800.8 | 2231.6 | 4.6 | a |
| G. d. T2 | 39621.0 | 1891.3 | 19.0 | a |

Treatments listed with different levels of significance (a or b) are statistically different from each other with $\alpha = 0.05$.

Inoculation resulted in increases in beet weight in 12 of the 14 strains compared to the control treatment. The greatest increases were achieved with G. diazotrophicus UAP AC7 (25.1%) and G. diazotrophicus PAL5T LsdB++ (24.5%). Averaged across all strains, the mean increase in shoot growth due to inoculation was 11.1%.

In comparing the data in Tables 10-13, and as was seen in the sand culture experiments (Tables 2-9), the effects of inoculation with Gluconacetobacter sp. varies with strain, plant part, and availability of $NO_3^-$ supplied to the sugar beet plants. As in the sand culture experiments, the greatest response to inoculation (41.3%) was found with strain G. diazotrophicus PAL5T LsdB++ in the beet at the lower level of $NO_3^-$ supply to the plant. Also as in the sand experiment (Table 7), the lowest average response to inoculation was seen in shoots at the higher (10 mM) level of $NO_3^-$ supply to the plants (Table 12). Again, the invention shows surprisingly that less nitrogen fertilizer is required. Also, the hypocotyl, which is the commercially important, harvestable portion of the plant, had stronger growth than other plant parts There were also differences in the trends of the results between the sand and natural soil experiments. Although in both experiments inoculation with Gluconacetobacter sp. had the greatest single effect on beet (hypocotyls) growth at the lower (2 mM) level of $NO_3^-$ supply to the plants, positive effects were seen in ten of the strains (Table 11) in the natural soil experiment, but occurred in six of the 14 strains tested in the sand experiment (Table 4). This may be indicative of the more "challenging" environment of the natural soil as compared to sand culture where competition from other soil microorganism will be less.

Example 2

Identification of Sites of Infection of Sugar Beet by Gluconacetobacter diazotrophicus The means by which Gluconacetobacter sp. is gaining entry (infecting) into sugar beet is analyzed. Specific infection sites by plant-growth-promoting-bacteria (PGPR) on host plants was determined by using a "labelled" version of the bacterium to view where it colonizes the plant. These labelled versions of PGPR have been genetically modified to contain a genetic sequence that under the proper conditions, leads to the production of a visible indicator of the location of the bacteria. An example of this is the β-glucuronidase or "GUS" marker (Jefferson R A, Burgess S M and Hirsh D. 1986. β-glucuronidase from Escherichia coli as a gene-fusion marker. Proc. Natl. Acad. Sci. USA. 83: 8447-8451) which when present in the genome of the bacterium, expressed by the bacterium, and provided with the proper staining conditions, results in the production of a blue colour to in the immediate vicinity of the bacterium.

A GUS-labelled version of G. diazotrophicus was used to show where the bacterium colonizes the plant soon after inoculation and thereby indicate where the bacterium is gaining access to infecting the plant roots.

Materials and Methods

Germinated sugar beet seeds were transplanted into 300 ml pots (one seedling per pot) containing sterilized sand and watered with sterilized, distilled water. Each seedling was inoculated with 5 ml LGI-P broth containing either G. diazotrophicus strains UAP-5541/pRGS561, or G. diazotrophicus PAL5T as control (optical density (OD) of 0.4 at 600 nm). The GUS-labeled strain contains a construct resulting in constitutive expression of a β-glucuronidase (GUS) gene (Fuentes-Ramirez, L. E.; Caballero-Mellado, J.; Sepulveda, J.; Martinez-Romero, E. Colonization of sugarcane by Acetobacter diazotrophicus is inhibited by high N-fertilization. Fed. Eur. Microbiol. Soc. Microbiol. Ecol. 29:117-128; 1999).

Seedlings were harvested either 4 or 7 days after inoculation and washed carefully to separate roots from the sand. Seedlings were then transferred into 5 ml clear vials. GUS activity was determined using the materials and protocols of the β-Glucuronidase Reporter Gene Staining Kit (Sigma-Aldrich, Inc., Oakville, Canada). Seedlings were fixed with 4% formaldehyde solution at room temperature for 45 minutes, washed three times with the washing solution, leaving the tissue in solution about 2-3 minutes each time. The staining solution (X-Gluc) was prepared 30 minutes before conducting the staining and keep at 4° C. Staining solution was added after washing and vials were degassed for 15 minutes in a vacuum desiccator. The vials were then covered with aluminum foil and placed in incubator at 37° C. in the dark for 12 hours. During the incubation, an insoluble blue colour is produced in tissues displaying GUS activity, which allows a histochemical localization of GUS activity. After incubation, chlorophyll is removed from the samples by desiccating the samples in an ethanol series of 25%, 35%, 50%, 70% and 90% for 30 min at each step. Stained samples were observed under a dissecting microscope and pictures were taken using Infinity Capture software (Lumenera Corp; Ottawa, Canada).

The results show that Gluconacetobacter colonized the root tip, the root hair and a lateral root intersection. The lateral root intersection is the portion of the root that is adjacent to the intersection formed by a root branch arising from a main root. Light micrograph of lateral root tips of sugar beet were taken 4 days after being inoculated with GUS-labelled Gluconacetobacter diazotrophicus UAP-5541/pRGS561. Root tip regions showed blue stain from GUS activity associated with colonization by G. diazotrophicus UAP-5541/pRGS561. Root hairs, typically mature root hairs, also showed blue stain. Light micrograph of lateral root of sugar beet 7 days after being inoculated with GUS-labelled Gluconacetobacter diazotrophicus UAP-5541/pRGS561 showed blue stain from GUS activity associated with colonization by G. diazotrophicus at the intersection of lateral roots.

Therefore, in an embodiment, the invention relates to a method for increasing the biomass of a sugar beet, comprising inoculating the sugar beet with the composition of claim 1 and growing the sugar beet, thereby obtaining increased biomass, wherein the *Gluconacetobacter* colonizes a portion of the root of the sugar beet, the portion comprising, consisting of, or consisting essentially of: a root tip, a root hair and/or a lateral root intersection. These method steps are also useful with other methods described in this application. Another aspect of the invention relates to a method for increasing the biomass of a sugar beet, comprising, consisting essentially of or consisting of: inoculating the sugar beet root tips, root hairs and/or root interface with *Gluconacetobacter* and growing the plant.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method for increasing the biomass of a sugar beet, comprising
   inoculating the sugar beet with a composition comprising:
   i) *Gluconacetobacter* in an effective amount to inoculate a sugar beet, and ii) an inoculation medium;
   growing the sugar beet, thereby obtaining increased biomass; and
   administering nitrogen fertilizer to the inoculated sugar beet, wherein the increased biomass is measured as increased biomass per unit of N-fertilizer applied to the inoculated sugar beet compared to a control sugar beet treated with the same amount of N-fertilizer but not treated with the composition.

2. The method of claim 1, wherein the inoculating comprises i) contacting the composition with the sugar beet or a sugar beet substrate proximate to the sugar beet so that the composition will contact the sugar beet in the substrate, or ii) contacting the composition with the sugar beet, sugar beet seed, soil surrounding the seed or root of the plant, or to a surface of a portion of the sugar beet that is above the substrate.

3. The method of claim 2, wherein the substrate is soil, sand or a hydroponic solution.

4. The method of claim 1, comprising inoculating the sugar beet at least 15 days after seeding.

SEQUENCE LISTING

<160> NUMBER OF SEQ ID NOS: 4

<210> SEQ ID NO 1
<211> LENGTH: 18
<212> TYPE: DNA
<213> ORGANISM: Gluconacetobacter diazotrophicus

<400> SEQUENCE: 1
ctgtttcccg caagggac                                              18

<210> SEQ ID NO 2
<211> LENGTH: 18
<212> TYPE: DNA
<213> ORGANISM: Gluconacetobacter diazotrophicus

<400> SEQUENCE: 2 gcgcccatt gctgggtt                                               18

<210> SEQ ID NO 3
<211> LENGTH: 17
<212> TYPE: DNA
<213> ORGANISM: Gluconacetobacter johannae

<400> SEQUENCE: 3
aatgactggg cgtaaag                                               17

<210> SEQ ID NO 4
<211> LENGTH: 18
<212> TYPE: DNA
<213> ORGANISM: Gluconacetobacter johannae

<400> SEQUENCE: 4
gaaatgaaca tctctgct                                              18

5. The method of claim 1, comprising inoculating the sugar beet after the first pair of sugar beet leaves open.

6. The method of claim 1, comprising inoculating the sugar beet after the cotyledon leaves are fully emerged but before true leaves are emerged.

7. The method of claim 1, comprising inoculating the sugar beet by applying the composition to a surface of a substrate around a stem of the sugar beet.

8. The method of claim 1, comprising growing the sugar beet at least until the sugar beet reaches harvestable maturity.

9. The method of claim 1, comprising growing the plant for at least 3 months from seeding.

10. The method of claim 1, wherein the nitrogen fertilizer contains a nitrogen concentration of 1 mM-10 mM.

11. A sugar beet inoculated in accordance with the method of claim 1.

12. The method of claim 2, wherein contacting the composition with the sugar beet seed comprises contacting at seeding or contacting by preinoculation prior to seeding.

13. The method of claim 12, wherein contacting at seeding comprises contacting the seed and/or the substrate surrounding the seed.

14. The method of claim 12, wherein said contacting at seeding comprises contacting the seed simultaneously with seeding in the substrate.

15. The method of claim 12, wherein said contacting by preinoculation prior to seeding comprises coating the seed with a polymer composition following inoculation.

16. The method of claim 1, wherein the *Gluconacetobacter* comprises *Gluconacetobacter diazotrophicus* or *Gluconacetobacter johannae*.

17. The method of claim 1, wherein said *Gluconacetobacter* comprises *Gluconacetobacter diazotrophicus* or *Gluconacetobacter johannae*, and wherein the inoculation medium comprises LGI-P, the LGI-P comprising biotin, pyridoxal salt and ammonium salt, and the LGP-1 free from yeast extract.

18. The method of claim 7, wherein said *Gluconacetobacter* is:
*Gluconacetobacter diazotrophicus* SRT4 LsdA−;
*Gluconacetobacter diazotrophicus* SRT4 LsdB++;
*Gluconacetobacter diazotrophicus* CFNE 550;
*Gluconacetobacter diazotrophicus* PSP 22;
*Gluconacetobacter diazotrophicus* SRT4;
*Gluconacetobacter diazotrophicus* PAL5T;
*Gluconacetobacter diazotrophicus* PAL5T LsdA−;
*Gluconacetobacter diazotrophicus* PAL5T LsdB++;
*Gluconacetobacter diazotrophicus* UAP AC7;
*Gluconacetobacter diazotrophicus* 1772;
*Gluconacetobacter diazotrophicus* T2;
*Gluconacetobacter johannae* UAP-Cf 51;
*Gluconacetobacter johannae* CFN-Cf 52; or
*Gluconacetobacter johannae* CFN-cf 76.

19. The method of claim 1, wherein the *Gluconacetobacter* has positive nitrogenase activity.

20. The method of claim 1, wherein the *Gluconacetobacter* in the composition is in a concentration of $10^3$ to $10^8$ CFU/Ml.

21. A method for increasing the biomass of a sugar beet, comprising:
inoculating the sugar beet with a composition comprising:
i) *Gluconacetobacter* in an effective amount to inoculate a sugar beet, and ii) an inoculation medium, wherein the *Gluconacetobacter* colonizes the interior of the sugar beet comprising the hypocotyl, shoot or root of the sugar beet.

22. The method of claim 21, wherein the *Gluconacetobacter* colonizes a portion of the root of the sugar beet, the portion comprising a root tip, a root hair or a lateral root intersection.

23. The method of claim 21, wherein the *Gluconacetobacter* in the composition is in a concentration of $10^3$ to $10^8$ CFU/Ml.

* * * * *

UNITED STATES PATENT AND TRADEMARK OFFICE
CERTIFICATE OF CORRECTION

PATENT NO. : 8,252,720 B2
APPLICATION NO. : 13/035252
DATED : August 28, 2012
INVENTOR(S) : J. Kevin Vessey et al.

It is certified that error appears in the above-identified patent and that said Letters Patent is hereby corrected as shown below:

In claim 18 at column 28, line 1, the number "7" in the reference to claim 7 should be changed to --1--.

Signed and Sealed this
Fifth Day of February, 2013

Teresa Stanek Rea
*Acting Director of the United States Patent and Trademark Office*